United States Patent [19]

Posner et al.

[11] Patent Number: 5,155,031

[45] Date of Patent: Oct. 13, 1992

[54] USE OF PERVANADATE AS AN INHIBITOR OF PHOSPHOTYROSINE PHOSPHATASE

[76] Inventors: Barry I. Posner, 360 Wood Ave., Westmount, Quebec, Canada, H3Z 1Z2; I. George Fantus, 4745 Meridian, Montreal, Quebec, Canada, H3W 2C2

[21] Appl. No.: 536,716

[22] Filed: Jun. 7, 1990

[51] Int. Cl.$^5$ .......................... C12N 9/99; C12N 1/38
[52] U.S. Cl. ..................................... 435/184; 435/244
[58] Field of Search ................................ 435/184, 244

[56] References Cited

U.S. PATENT DOCUMENTS

| | | | |
|---|---|---|---|
| 3,755,232 | 8/1973 | Rodaway et al. | 524/552 |
| 4,710,469 | 12/1987 | Liang et al. | 435/194 |
| 4,882,171 | 11/1989 | Posner et al. | 514/866 |

OTHER PUBLICATIONS

Lau et al, *Vanadate Stimulates Bone Cell Proliferation . . .*, Endocrinology, vol. 123, No. 6, 1988.
Marshall et al, *Down-Regulation of Cell Surface . . .*, Endocrinology, vol. 121, No. 3, 1987.
Yonemoto et al, *Detection of Phosphotyrosine . . .*, Mol.& Cell. Biology, vol. 7, No. 2, 1987.
Fantus et al., *Pervanadate [Peroxides of . . .*, Biochemistry, vol. 28, No. 22, 1989.
Hildebrand et al, *Principles of Chemistry*, pp. 362-364, 1952.
Kadota et al, *Peroxide of Vanadium: A Novel . . .*, Biochemical and Biophysical Research Comm., vol. 147, No. 1, 1987.
Kadota et al, *Stimulation of Insulin-like . . .*, J. of Biol. Chem., vol. 262, No. 17, pp. 8252-8256, 1987.
Zick et al, *A Combination of $H_2O_2$ and Vanadate . . .*, Biochemistry, vol. 29, pp. 10240-10245, 1990.
Heffetz et al, *The Insulinomimetic Agents . . .*, J. of Biol. Chem., vol. 265, No. 5, pp. 2896-2902, 1990.

*Primary Examiner*—David M. Naff
*Assistant Examiner*—Mike Meller
*Attorney, Agent, or Firm*—Robic

[57] ABSTRACT

Disclosed is a method of inhibiting phosphotyrosine phosphatase activity on a substrate which comprises preincubating the substrate with a pervanadate-containing solution. Also disclosed is the use of a solution comprising pervanate as an inhibitor of phosphotyrosine phosphatases and as a regulator of cell growth.

9 Claims, 3 Drawing Sheets

Inhibitory effect of increasing doses of:

(▲) vanadate, and (•) pervanadate.

1  2  3  4  5  6

94 kDa ⟶

Hepatic Phosphatase  $\underbrace{+\ +\ -\ -}_{H_2O_2(10^{-4}M)}\ \underbrace{+\ +}_{pV(10^{-4}M)}$ Lanes 1-4: $10^{-4}$ M $H_2O_2$; lanes 5 and 6: $10^{-4}$ M catalase-treated pervanadate.

1  2  3  4  5  6  7  8  9  10  11  12

94 kDa ⟶

Hepatic Phosphatase  $\underbrace{-\ -\ +\ +}_{C}\ \underbrace{-\ -\ +\ +}_{V(10^{-4}M)}\ \underbrace{-\ -\ +\ +}_{V(10^{-4}M)+H_2O_2(10^{-4}M)}$ Effect of exposure of adipocytes to pervanadate on insulin receptor autophosphorylation. The values are expressed as percent of maximum densitometry measured in arbitrary units.

USE OF PERVANADATE AS AN INHIBITOR OF PHOSPHOTYROSINE PHOSPHATASE

BACKGROUND OF THE INVENTION

1. Field of the Invention

The present invention relates to the use of pervanadate as a potent inhibitor of phosphotyrosine phosphatase with a distinct specificity from previously described inhibitors.

This invention also relates to the use of such a particular property and specification of pervanadate provide a potentially useful agent for regulation of cell growth.

2. Brief Description of the Prior Art

Vanadate on the one hand, and hydrogen peroxide ($H_2O_2$) on the other hand, are well documented to mimic the actions of insulin. Recent interest in vanadate has increased since it has been demonstrated to increase the tyrosine kinase activity of the insulin receptor (Tamura et al., J. Biol. Chem. 259, 6650–6658, 1984), and it has been used successfully in short-term treatment of streptozotocin-induced diabetic rats (Heyliger et al., Science 227, 1474–1477, 1985; Meyerovitch et al., J. Biol Chem. 262, 6658–6662, 1987). It has also been demonstrated that a mixture of vanadate and $H_2O_2$ produced a synergistic effect to augment IGF-II (insulin-like growth factor II) binding to rat adipocytes and to activate the insulin receptor kinase (Kadota et al., J. Biol. Chem. 262, 8252–8256 1987).

The efficacies of the mixture of vanadate and $H_2O_2$, of each agent alone, and of insulin to increase IGF-II binding have proved to be correlated with their respective efficacies to activate the insulin receptor tyrosine kinase in an in situ intact cell assay (Kadota et al., Supra). It has also been demonstrated that the synergistic insulin-like effect of vanadate mixed with $H_2O_2$ was due to the generation of peroxide(s) of vanadate which are termed pervanadate (Kadota et al., Biochem. Biophys. Res. Commun 147, 259–266, 1987). In this study, it has also been disclosed that addition of catalase abolishes the synergism only if it is made at the same time as the vanadate and $H_2O_2$. However, such an addition does not abolish the synergism 10 min. after mixing of the two agents. It is disclosed that pervanadate stimulates in situ tyrosine phosphorylation of the insulin receptor in adipocytes with maximal effects similar to that of insulin. Concomitant with enhanced tyrosine phosphorylation, pervanadate activates the insulin receptor kinase but with a slower time course than insulin.

The inbibition of insulin receptor β-subunit tyrosine dephosphorylation by pervanadate and lack of in vitro stimulation of autophosphorylation or tyrosine kinase activity suggest that this insulin-mimetic agent acts via inhibition of specific tyrosine phosphatase(s).

OBJECTS OF THE INVENTION

On the basis of this suggestion, an object of the present invention is to provide a method of inhibiting phosphotyrosine phosphatase activity, using pervanadate to do so.

Another object of the present invention is to use pervanadate as an inhibitor of phosphotyrosine phosphatase and as a regulator of cell growth.

SUMMARY OF THE INVENTION

More particularly, the present invention provides a method of inhibiting phosphotyrosine phosphatase activity on a substrate which comprises pre-incubating the substrate with a pervanadate-containing solution.

This invention is also concerned with the use of a solution comprising pervanate as an inhibitor of phosphotyrosine phosphatases and as a regulator of cell growth.

DETAILED DESCRIPTION OF EMBODIMENTS

The present invention is based on the discovery that pervanadate activates the tyrosine kinase in intact cells by potently inhibiting phosphotyrosine phosphatase.

The vanadate solution used in the examples presented below was prepared as described in Kadota et al. supra, to avoid changes in pH and the generation of colored decavanadate (orange-yellow) or vanadyl ion, $VO^{2+}$(blue). The solution of pervanadate was prepared by mixing vanadate or vanadate containing substance with $H_2O_2$ or a peroxide-containing substance ($10^{-3}$ M unless otherwise indicated) for 15 min at 22° C. This was followed by the addition of catalase, 200 μg/mL, to remove residual $H_2O_2$. This procedure resulted in the generation of a peroxidized form of vanadate which is stable for 2 h without further addition of $H_2O_2$. The concentration of pervanadate generated is denoted by the vanadate concentration added to the mixture.

The vanadate and vanadate containing substance used in the above preparation may be any kind of alkaline-earth metal vanadate or alkali metal vanadate and more particularly of sodium vanadate. The peroxide-containing substance may be selected from ethyl peroxide or pyridine peroxide although use is preferably made of hydrogen peroxide.

Advantageously, the concentrations of the starting compounds are selected so that the concentration of pervanadate in the solution ranges from $10^{-7}$ to $10^{-3}$ molar.

Example 1

To establish the above mentioned activity the effect of pervanadate on alkaline phosphatase catalyzed dephosphorylation of the lectin-purified insulin receptor was evakyated.

Figure 1:
FIG. 1 is an autoradiogram illustrating the effect of pervanadate on alkaline phosphatase-catalyzed dephosphorylation of a purified insulin receptor after submitting the samples to SDS-PAGE and radioautography.

To do so, lectin-purified insulin receptor (6.0 fmol of insulin binding) was preincubated with $10^{-7}$ M insulin for 60 min at 4° C. Phosphorylation was initiated by addition of [γ-$^{32}$P]ATP, and the insulin receptor was immunoprecipitated by incubating with anti-insulin receptor antibody (140 μg of protein) for 4h at 4° C. followed by incubation with protein A-SEPHAROSE * beads for 1 h at 4° C. The immunoprecipitate was washed twice with 50 mM HEPES buffer, pH 7.6, containing 0.1% TRITON X-100 * detergent and 0.1% SDS and once with the above buffer without SDS. After being washed, the immunoprecipitate was incubated with or without the indicated concentrations of vanadate, H$_2$O$_2$, or pervanadate in the presence or absence of a 15 units.mL solution of alkaline phosphatase for 60 min at 4° C. with vigorous shaking. This sample was washed twice with 50 mM HEPES buffer, pH 7.6, containing 0.1% TRITON X-100 * detergent and subjected to SDS-PAGE followed by radioautography as shown in FIG. 1. Densitometric scanning of the radioautographs was done with a ZEINER * soft laser scanning densitometer (Model SL-504-XL).

* Trade-mark

Figure 2:
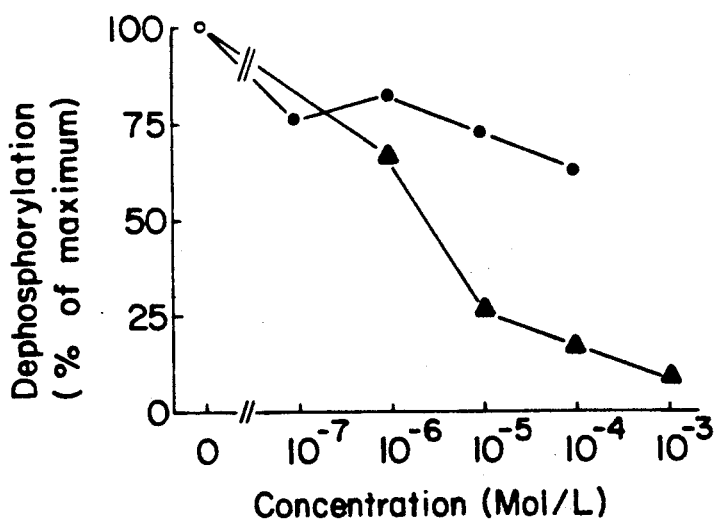
FIG. 2 is a dose-response curve illustrating the effects of pervanadate and vanadate on alkaline phosphatase-catalyzed dephosphorylation of a purified insulin receptor.

Alkaline phosphatase clearly dephosphorylates the $^{32}$P-labeled insulin receptor β-subunit (FIG. 1, lanes 1 and 2). The inhibitory effect of increasing concentrations of vanadate and pervanadate on the extent of β-subunit dephosphorylation (FIG. 1, lanes 3-7 and 10-14) is summarized in FIG. 2. Vanadate inhibited the dephosphorylation of the $^{32}$P-labeled insulin receptor in a dose- dependent manner. In contrast, the inhibition by pervanadate was much less than that by vanadate alone. Also, $10^{-3}$ M H$_2$O$_2$ alone was without effect (FIG. 1, lanes 8 and 9).

Example 2

Since vanadate and pervanadate may have different specificities for various phosphoprotein phosphatases, their inhibitory effects were separated tested on insulin receptor tyrosine dephosphorylation catalyzed by a crude preparation of phosphotyrosine phosphatase activity extracted from rat liver microsomes.

The samples were processed as in example 1, except that after being washed, the immunoprecipitate was incubated with or without $10^{-4}$M vanadate, $10^{-4}$M H$_2$O$_2$ or $10^{-4}$m pervanadate in the presence or absence of an equal volume, 50 μL, of rat hepatocyte phosphotyrosine phosphatase (as described above) for 20 min at 30° C. with vigorous shaking.

Figure 3:
FIG. 3 is an autoradiogram illustrating the effect of vanadate and the mixture of vanadate and peroxide on rat hepatocyte tyrosine phosphatase-catalyzed dephosphorylation of the insulin receptor after submitting the samples to SDS-PAGE and radioautography.
Figure 4:
FIG. 4 is an autoradiogram illustrating the effect of pervanadate on rat hepatocyte tyrosine phosphatase-catalyzed dephosphorylation of the insulin receptor after submitting the samples to SDS-PAGE and radioautography.

In contrast to the above results, catalase-treated pervanadate powerfully inhibited tyrosine dephosphorylation (FIG. 3, lanes 5 and 6), while H$_2$O$_2$ (FIG. 3, lanes 1-4) was without effect. In this case, vanadate also inhibited dephosphorylation but with less efficacy (FIG. 4, lanes 5 to 8) then pervanadate not treated with catalase (FIG. 4, lanes 9 to 12).

Example 3

To elucidate further the mechanism of action of pervanadate, this compound was added in vitro to solubilized WGA-purified adipocyte insulin receptors.

Isolated rat adipocytes were incubated with different concentrations of pervanadate ($10^{-3}$ to $10^{-7}$M), 10 ng/mL ($1.7 \times 10^{-9}$M) insulin, or no additions for 15 min at 37° C. Insulin receptors were solubilized and partially purified by WGA chromatography. An aliquot of insulin receptor purified by WGA chromatography. An aliquot of insulin receptor (5-10 fmol of insulin binding) was used in the autophosphorylation assay as described below, in the presence or absence of in vitro insulin, followed by SDS-PAGE and radioautography.

Figure 5:
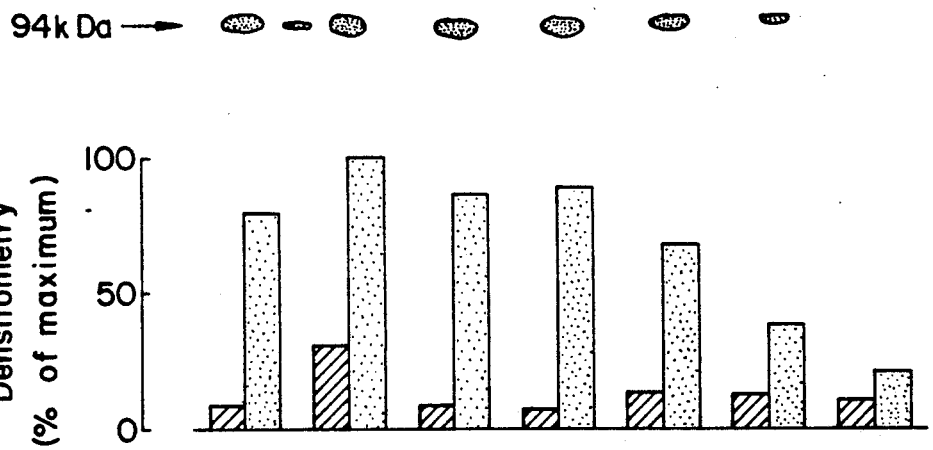
FIG. 5 is an autoradiogram illustrating the effect of exposure of adipocytes to pervanadate on insulin receptor autophosphorylation as expressed in a % of maximum phosphorylation.

The Insulin Receptor Autophosphorylation Assay proceeded as follows: lectin-purified insulin receptor (5-10 fmol of insulin binding) was incubated with or without $10^{-7}$ M insulin in a 50 mM HEPES buffer containing 8 mM MnCl$_2$, 10 mM MgCl$_2$, 270 μM dithiothreitol, and 10 μg/mL bovine serum albumin for 1 h at 4° C., in a total volume of 90 μL. The phosphorylation reaction was initiated by the addition of 10 μL of diluted [γ-$^{32}$P]ATP (10 Ci/mmol) to a final concentration of 50 μM, and the reaction mixture was further incubated for 15 min at 4° C. The reaction was terminated by adding 50 uL of 50 mM HEPES buffer, pH 7.4, containing 0.24% TRITON X-100*$^{detergent}$, 23 mM EDTA, 24 mM sodium pyrophosphate, 2mM PMSF, and 24 nM APT. The insulin receptor was immunoprecipitated as described in example 1. * TM In contrast to insulin (FIG. 5, lanes 1 to 4), pervanadate did not significantly stimulate autophosphorylation (FIG. 5 lanes 5-14). It has already been established that pervanadate does not either stimulate autophosphorylation of exogenous tyrosine kinase activity (Kadota et al., Biochem. Biophys. Res. Comm. 147, 259-266, 1987). Vanadate itself has been documented to inhibit tyrosine phosphatases (Swarup et al., Biochem. Biophys. Res. Comm. 107m 1104-1109, 1982). This may account for its weak insulin-mimetic effects. It was found that pervanadate does not inhibit alkaline phosphatase catalyzed dephosphorylation of the insulin receptor. However, pervanadate has proved to be a potent inhibitor of insulin receptor tyrosine dephosphorylation catalyzed by an endogenous rat liver phosphoprotein phosphatase. In the latter case, pervanadate is more efficacious than vanadate. The lack of in vitro stimulation of the insulin receptor kinase, the slower time course of activation in intact cells as compared to insulin, and the inhibition of tyrosine dephosphorylation of the labeled receptor all strongly suggest that the mechanism of action of pervanadate involves primarily the inhibition of a specific phosphotyrosine phosphatase.

It is believed that growth in cells is dependent on tyrosine phosphorylation in specific proteins. Phosphotyrosine phosphatases reduce this level of phosphotyrosine accumulation in specific proteins and hence, may act as regulators of cellular growth. Agents which inhibit these enzymes may allow such phosphorylation to occur more readily and to a greater extent, and hence may promote cellular growth. Thus, pervanadate compounds might find a specific use in promoting cell growth via the mechanism of inhibition of phosphotyrosine phosphatase.

What is claimed is:

1. A method of inhibiting phosphotyrosine phosphatase activity on a substrate, which comprises preincubating said substrate with a pervanadate containing solution.

2. A method according to claim 1, wherein the concentration of pervanadate ranges from about $10^{-7}$ moles/liter of solution to $10^{-3}$ moles/liter of solution.

3. A method according to claim 1, wherein said preincubation is performed for about 20 to 60 min. at a temperature from about 4 to 30° C.

4. A method according to claim 3, wherein the pervanadate is the reaction product of a vanadate containing substance with a peroxide containing substance.

5. A method according to claim 4, wherein the vanadate is selected from the group consisting of: alkaline earth metal vanadate, and alkali metal vanadate.

6. A method according to claim 5, wherein the vanadate is sodium vanadate.

7. A method according to claim 4, wherein the peroxide is selected from the group consisting of: ethyl peroxide, and pyridine peroxide.

8. A method according to claim 4, wherein the peroxide is hydrogen peroxide.

9. A method according to claim 3, wherein the concentration of pervanadate ranges from about $10^{-7}$ moles/liter of solution to $10^3$ moles/liter of solution.

* * * * *